United States Patent
Van Schie et al.

(10) Patent No.: US 6,818,244 B2
(45) Date of Patent: Nov. 16, 2004

(54) DIACETYL TARTARIC ACID ESTERS OF MONO- AND DIGLYCERIDES BASED ON C12 TO C22 FATTY ACIDS

(75) Inventors: Bartholomeous Jozef Van Schie, Huizen (NL); Peter Johannes Coenders, Dordredl (NL); Pieter Hendrik Paul Stegeman, Garland (NL); Johannes Durk Gombert, Velp (NL); Martin Robert Roest, Huizen (NL)

(73) Assignee: Quest International B.V., Utrecht (NL)

( * ) Notice: Subject to any disclaimer, the term of this patent is extended or adjusted under 35 U.S.C. 154(b) by 17 days.

(21) Appl. No.: 10/340,588

(22) Filed: Jan. 13, 2003

(65) Prior Publication Data

US 2003/0162893 A1 Aug. 28, 2003

Related U.S. Application Data

(62) Division of application No. 09/474,762, filed on Dec. 30, 1999, now Pat. No. 6,642,278.

(30) Foreign Application Priority Data

Dec. 30, 1998 (EP) ............................................. 98204487

(51) Int. Cl.$^7$ ................................................ A21D 13/00
(52) U.S. Cl. ...................... 426/549; 426/553; 426/601; 516/29; 516/73; 560/180
(58) Field of Search ................................ 426/604, 549, 426/601, 556, 553; 516/29, 73; 560/180

(56) References Cited

U.S. PATENT DOCUMENTS

| | | | |
|---|---|---|---|
| 2,938,027 A | 5/1960 | Gladstone | |
| 3,141,030 A | 7/1964 | Buddemeyer et al. | |
| 3,180,736 A | 4/1965 | Landfried | |
| 3,223,532 A | 12/1965 | Pinkalla et al. | |
| 3,623,887 A | 11/1971 | Buddemeyer et al. | |
| 5,254,356 A | 10/1993 | Busken | |
| 6,130,257 A | 10/2000 | Coenders et al. | |
| 6,635,299 B1 * | 10/2003 | Van Schie et al. | .......... 426/556 |

FOREIGN PATENT DOCUMENTS

| | | |
|---|---|---|
| GB | 1 220 488 | 1/1971 |
| GB | 1 344 518 | 1/1974 |

* cited by examiner

*Primary Examiner*—Lien Tran
(74) *Attorney, Agent, or Firm*—Fitch, Even, Tabin & Flannery

(57) ABSTRACT

The invention provides baked products incorporating a mixture comprising diacetyl tartaric acid esters on mono- and diglycerides based on C12 to C22 fatty acids, wherein the mixture contains diacetyl tartaric acid glycerol monoesters that contain:

(A) one fatty acid group, one diacetylated tartaric acid monoester groups and a free hydroxyl group and (B) one fatty acid group and two diacerylated tartaric acid monoester groups in which the molar percentages of (A) and (B) obtained by a specific NMR-technique which satisfies certain defined parameters.

13 Claims, 1 Drawing Sheet

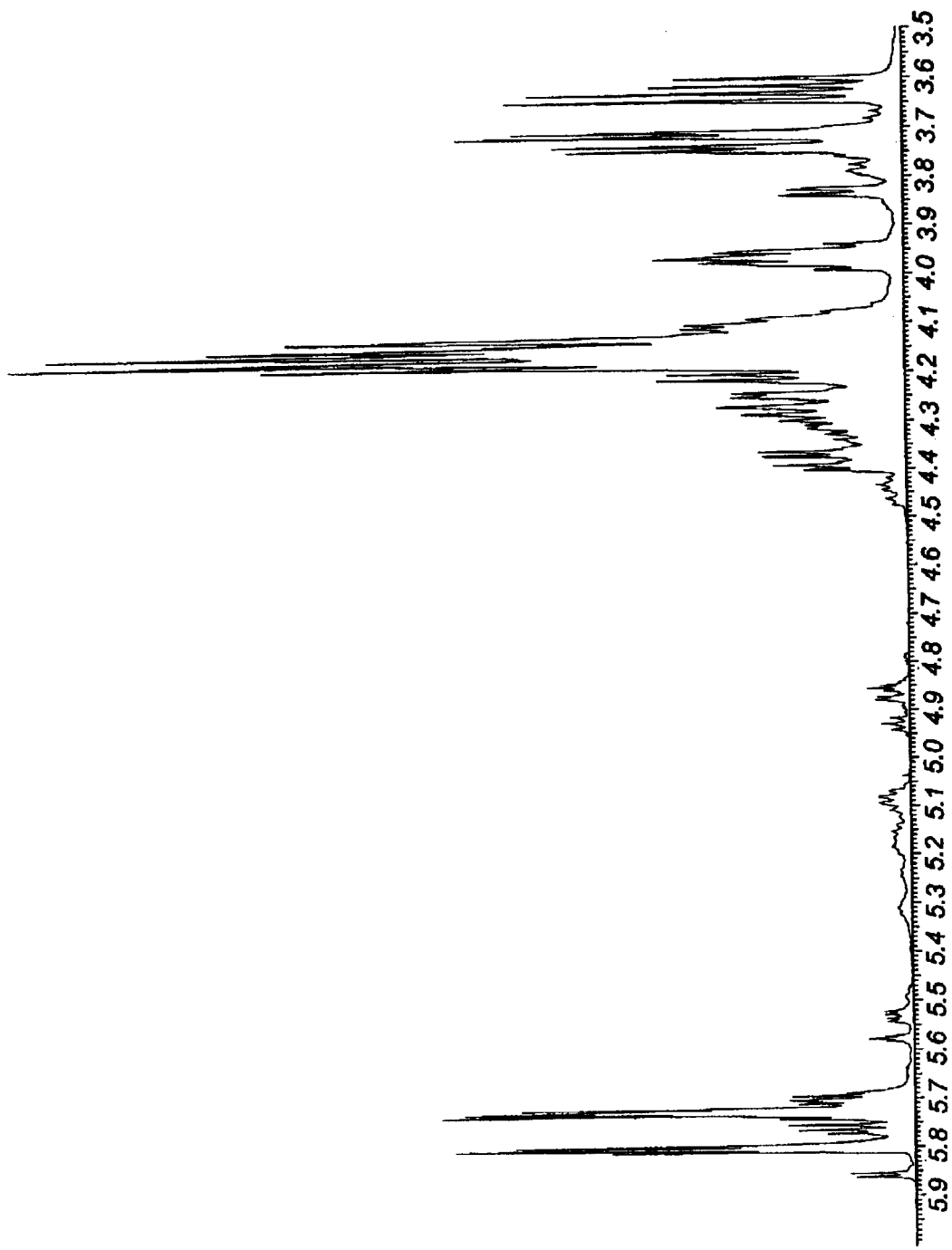

DIACETYL TARTARIC ACID ESTERS OF MONO- AND DIGLYCERIDES BASED ON C12 TO C22 FATTY ACIDS

RELATED APPLICATIONS

This is a divisional application of our U.S. application Ser. No. 09/474,762, filed Dec. 30, 1999 now U.S. Pat. No. 6,642,278 which designated the United States and claims the priority benefit of EP 98204487.7, filed Dec. 30, 1998, the disclosures of which are incorporated by reference.

FIELD OF THE INVENTION

The invention relates to a mixture comprising diacetyl tartaric acid esters of mono- and diglycerides based on C12 to C22 fatty acids. Diacetyl tartaric acid esters of mono- and diglycerides based on C12 to C22 fatty acids are generally known as baking ingredients for baked products. More particularly, they are generally known for yeast-leavened products such as bread (especially white bread), tin bread, rolls, hard rolls, German crispy rolls, buns, rusks etc. These esters are able to improve the products in various respects as good leavening expressed as specific volume; even pores and acceptable crustiness. They are also known to improve the properties of dough such as its stability and rheology and are therefore often referred to as dough conditioners. The esters are further used in baking aids and in improved flour. The ED number of mixtures of diacetyl tartaric acid esters of mono- and diglycerides based on C12 to C22 fatty acids is E472e (DATEM).

BACKGROUND OF THE INVENTION

The art has long described mixtures comprising diacetyl tartaric acid esters of mono-and diglycerides based on C12 to C22 fatty acids and their preparation. U.S. Pat. No. 2,236,516 (Frank J. Cahn et al) is an early patent specification disclosing products obtained by reacting diacetyl tartaric acid with glyceryl monostearate. U.S. Pat. No. 2,689,797 (Morris H. Joffe) discloses improvements in bread obtained by the incorporation of diacetyl tartaric esters of unsaturated and partially saturated mono and/or partial glycerides. U.S. Pat. No. 2,938,027 (Martell M. Gladstone) discloses the reaction between mixtures of acetylated anhydrides of food acids such as e.g. tartaric acid containing 4 to 95% of diacetylated tartaric acid and e.g. free acetic anhydride with partial glycerides of fatty acids to obtain improved products. U.S. Pat. No. 3,443,969 (Nobuo Nakejima et al) discloses diacetyltartaric esters of purified (molecular distilled) monoglycerides of vegetable oils. GB-A-1,220,488 (Aktieselskabet Grindstedvaerket) discloses the preparation of an emulsifier obtained by reacting, e.g., distilled glycerol monostearate with diacetyl tartaric anhydride in certain molar ratios followed by prolonged heating to 135–190° C. as to obtain by polymerization a satisfactory oil-in-water emulsifier of higher molecular weight, which apparently contains polymeric esters due to splitting off acetic acid and water. GB-A-1,344,518 (Dynamit Nobel A.G.) discloses solid acetyltartaric esters obtained by reacting at least partially acetylated tartaric acid with partial glycerides containing 55–65% monoglyceride and an iodine value below 5 which contain per mole of partial glyceride 0.91–1.8 mole tartaric acid residues and 1.8–3.4 mole acetic acid residues. These esters are free flowing powders whereas the traditional esters have a waxy or honey-like consistency. This difference in physical properties is due to the fact that these powders contain appreciable quantities of say about 0.3 mol % of glyceride esters of monoacetyl tartaric residues and/or even non-acetylated tartaric acid residues. Conventional acetylated tartaric acid esters of mono- and/or diglycerides are mono- and/or diglyceride esters of (almost) pure diacetylated tartaric acid (anhydride). The products according to the present invention are also very low in esters of monoacetylated tartaric acid (anhydride).

Although the current diacetyl tartaric acid esters of mono- and diglycerides based on C12 to C22 fatty acids are valuable products they are often somewhat defective as to:

1. specific volume of the baked product obtained;
2. stability as to leavening under the influence of yeast; and/or
3. stability properties of the dough prepared.

SUMMARY AND OBJECTS OF THE INVENTION

It is an object of the present invention to provide a mixture comprising diacetyl tartaric acid esters of mono- and diglycerides based on C12 to C22 fatty acids yielding a performance which is improved in at least one of the properties mentioned above. Moreover, the present invention also provides a process for the preparation of the aforementioned mixture(s) of the diacetyl tartaric acid esters of mono- and diglycerides based on C12 to C22 fatty acids by reaction of diacetylated tartaric acid anhydride and mono- and diglycerides C12 to C22 fatty acids at a relatively low temperature combined with a short reaction time, which is more economical than most of the current processes.

BRIEF DESCRIPTION OF THE DRAWING

The FIGURE is a plot from a NMR.

DETAILED DESCRIPTION OF THE INVENTION

The invention therefore provides in a first embodiment a mixture comprising diacetyl tartaric acid esters on mono- and diglycerides based on C12 to C22 fatty acids. The mixture comprises diacetyl tartaric acid glycerol monoesters containing: (A) one fatty acid group, one diacetylated tartaric acid monoester group and a free hydroxyl group and (B) one fatty acid group and two diacetylated tartaric acid monoester groups, wherein 1. the concentration of (A) above in the total mixture, obtained by dividing the molar amount of (A) by the sum of the molar amounts of all components in the mixture and multiplying by 100, is at least 45%, preferably at least 50%, and
2. the fraction obtained by dividing the molar amount of (A) above by the combined molar amounts of (A) and (B) taken together is at least 0.70, preferably at least 0.72 and in which the molar amounts are determined by the NMR method herein described.

These NMR measurements were performed at 50° C. in $CDCl_3$ on a Jeol JNMR EX400 FT-NMR spectrometer operating at 400 MHz for $^1H$. Typically, 20 mg of sample was dissolved in 0.5 ml of solvent. To prevent overlap of the $H_2O$ resonance with resonances of the product, the pH of the sample was lowered to approximately 4 by adding acetic acid. The pulse delay (PD) time had to be chosen such that full relaxation of the signals takes place ($PD > 5T_1$).

The contents of (A) and (B) (mol %) can be calculated from the integral values:

P: δ=4.0 ppm to 4.5 ppm
Q: δ=4.7 ppm to 4.9 ppm
R: δ=5.0 ppm to 5.2 ppm
S: δ=5.2 ppm to 5.4 ppm,
e.g from the graph as illustrated in FIG. 1 by the formulae:

$$(A) = \left[ \frac{\frac{P - (4Q + 2R + 4S)}{5}}{P' + Q + R + S} \right] \cdot 100 [\text{mol \%}]$$

$$(B) = \left[ \frac{S}{P' + Q + R + S} \right] \cdot 100 [\text{mol \%}]$$

$$P' = \frac{P - (4Q + 2R + 4S)}{5}$$

N.B. All these integral values have to be corrected for glycerol mono-, di- and triesters of C14 to C18 fatty acids, if any, first.

Or, in words, in the formulae:

(A) equals a fraction of which the numerator is 100 times (P minus the sum of 4 times Q plus twice R plus 4 times S) divided by 5 and the denominator is (the sum of P' plus Q plus R plus S in which P' is P minus the sum of 4 times Q plus twice R plus four times S) divided by 5; and (B) equals a fraction of which the numerator is S multiplied by 100 and the denominator is (the sum of P' plus Q plus R plus S in which P' is P minus the sum of 4 times Q plus twice R plus four times S) divided by 5.

In case a product is at stake which contains fatty acid triglyceride as an extender as may be the case the NMR data measured need to be corrected for this percentage of triglyceride. Therefore the amount of triglyceride, if present, has to be determined and the method disclosed by P. Quinlan and H. J. Weiser Jr in JAOCS 35, 325–6 (1958) was found suitable. We used a modified method employing toluene (technical grade) instead of benzene and silicagel 60, no 1.07734.110 cx Merck, 20–230 mesh which activated with 9 wt % of water instead of 5% of water. The NMR signals of the specific fatty acid triglycerides which are needed are known from Sadtler Index of 1 H-NMR spectra (Sadtler Research Laboratories (Biorad) Philadelphia, Pa., USA).

In case a product is at stake in which mono- and/or diglycerides are used as an extender, the analysis of the percentage diglycerides was carried out by proton NMR applying the same method as used for the determination of A and B above. 1–2 diglycerides were measured at δ=4.30 ppm, and 1–3 diglycerides were measured at δ=4.05 to 4.25 ppm. Both components were calculated with formula:

$$\text{Mol \% Diglycerides} = \frac{I_{4.30}}{P' + Q + R + S}$$

Since 1–3 diglycerides interfere with A, a mathematical correction had to be applied. The basis for this correction is the known fixed ratio between 1–2 and 1–3 diglycerides of 40:60 wt %. From literature (JAOCS 37; August 1960 and JAOCS 23, 390 (1960)) a general ratio from 35:65 to 49:51 depending on the chain length (C12–C18) and temperature (20–200° C.) of the fatty acids is known. Since in most commercial emulsifiers the majority of fatty acids used are of C16 and C18 chain length, a 1–2, 1–3 diglycerides ratio of 2:3 was been applied. In case diglycerides were present as indicated at δ=4.30 ppm, the integral P has to be corrected by subtracting two and a half times the integral value of 1–2 diglycerides at δ=4.30 ppm.

The integral value for triglycerides has been calculated according to:

$$I_{Tri} = \frac{G \cdot I_A \cdot M_A + G \cdot I_B}{(1 - G) \cdot M_{Tri} + G \cdot M_B}$$

wherein G is the weight fraction triglycerides determined using the modified method of Quinlan and Weiser in JAOCS 1958 cited above, $M_A$, $M_B$ and $M_{Tri}$ the average molecular masses of components A, B and triglycerides respectively and $I_A$ and $I_B$ the integral values obtained by NMR for components A and B including triglycerides.

Mono-diglycerides of C12–C22 fatty acids which can be used in the preparation of the mixtures of diacetyl tartaric acid esters of mono- and diglycerides based on C12 to C22 fatty acids according to the present invention are obtainable from triglycerides of these fatty acids which can be of both vegetable and animal origin, e.g., from soya bean oil, coconut oil, babussa oil, palm oil, sunflower oil, lard, tallow and fish oil, optionally hydrogenated or fractionated. Mixtures of mainly palmitic and stearic acid are preferred. The mono-diglycerides can be prepared by interesterification with glycerol, usually in the presence of an alkaline catalyst. Mostly the triglyceride oil and the glycerol reacted are free from water or moisture. Further details of this reaction are disclosed in, for example, U.S. Pat. No. 2,875,221 (Bimbaum). Esterification leads to mixtures of mono- and diglycerides. After removal of water and unreacted glycerol the product obtained contained up to 65 wt % of monoglycerides. More pure monoglycerides can be obtained by molecular distilling the monoglycerides from the mixture and results in monoglycerides containing at least 90% monoglycerides. Such distilled products are e.g. marketed under the tradename Hymono ex Quest, Naarden, Netherlands. Crystallization and other fractionation processes might also yield similar relatively pure products. The term distilled monoglycerides therefore here has a wider interpretation than the literal sense and covers also purified monoglycerides obtained by other means than distillation. Monoglycerides containing 60 to 80% monoglycerides are usually prepared by diluting distilled monoglycerides with undistilled mono-diglycerides. They are marketed as such and in admixture with triglyceride fat. Monoglycerides containing from 60, preferably 70, to 99, more preferably 80 to 99 wt % of monoglyceride can be used for preparing the present mixtures. In the practice of the present invention it is preferred to use distilled products especially those obtained by molecular or short path distillation.

Diacetylated tartaric acid anhydride and derivatives are usually prepared from tartaric acid (dextro, levo, racemic or meso), preferably from natural=L–(+) tartaric acid or racemic tartaric acid and excess acetic anhydride by heating in the presence of suitable catalyst like sulphuric acid and distilling of acetic acid. The diacetylated tartaric acid (anhydride) used in the practice of the present invention is substantially diacetylated material and contains less than 2.5 mol %, preferably less than 1 mol %, more preferably less than 0.5 mol % of monoacetylated material. Further details are disclosed, for example, in U.S. Pat. No. 2,520,139 (Fuchs) and WO 96/35658 (Quest International) especially for D- and DL-tartaric acid as starting materials. It is normal practice to use food grade or P.A. grade materials in the preparation. In another embodiment of the invention the novel mixture of diacetylated tartaric acid esters of mono-and/or diglycerides described above is diluted with a suitable edible and/or food grade extender (e.g. fatty acid triglyceride or mono- and/or diglyceride of fatty acid(s) or another emulsifying agent) to any cost-effective level at which improved baking properties are still noticeable. Usually the amount of extender ranges between 10 and 50, preferably 20 and 40 wt % in the diluted product.

In a preferred embodiment the invention provides a mixture, in which the concentration of (A) above in the mixture, obtained by dividing the molar amount of (A) by the sum of the molar amounts of all components in the mixture and multiplying by 100 is at least 55%, preferably at least 60% (or e.g at least 65%).

In another preferred embodiment the invention provides a mixture as specified above in which the fraction obtained by dividing the molar amount of (A) above by the combined molar amounts of (A) and (B) taken together is at least 0.75, preferably at least 0.85 (or, e.g., at least 0.90).

In another preferred embodiment the invention provides a mixture as specified above in which the reaction mixture is based on distilled monoglycerides and contains less than 5, preferably less than 4 wt % of diacetyl tartaric esters of fatty acid diglycerides.

In another preferred embodiment the invention provides a mixture as specified above in which the mixture is based on mono- and diglycerides of substantially fully saturated C16 and/or C18 fatty acids.

In another embodiment the invention provides a process for preparing a novel mixture comprising diacetyl tartaric acid esters of mono- and diglycerides based on C12 to C22 fatty acids as described above in which diacetylated tartaric acid anhydride is molten and reacted at 135–175° C. with molten C12 to C22 fatty acid partial glycerides comprising 60–99, preferably 70 to 99 wt %, of monoglycerides, preferably in an inert atmosphere, for a reaction period of from 0.5 to 30, preferably from 1 to 15 minutes, more preferably from 2 to 10 minutes in the presence of an effective amount of a catalyst. Suitable catalysts are, e.g., alkaline compounds like sodium, potassium, magnesium or calcium carboxylates such as their stearates, palmitates and other carboxylic acid salts, e.g., in amounts from 0.05 to 0.5 wt percent calculated on the reaction mixture.

In another embodiment the invention provides a process for preparing a process for preparing a novel mixture comprising diacetyl tartaric acid esters of mono- and diglycerides based on C12 to C22 fatty acids, more preferably based on saturated C16 to C18 fatty acids as described above, in which the mono-diglycerides containing 60 to 99, preferably 70 to 99 wt. % of monoglycerides are molten and solid diacetylated tartaric acid anhydride is dissolved therein and reacted in the liquid phase, preferably in an inert atmosphere, with the mono-diglycerides at a temperature between 60° C. and 120° C. for a period of 5 to 30 minutes in the presence of an effective amount of an alkaline catalyst. This reaction usually takes place frilly in the liquid phase.

The preparation of mixtures of diacetyl tartaric acid esters of mono- and diglycerides based on C12 to C22 fatty acids according to the present invention can be carried out batchwise (e.g. in a stirred tank reactor), semi-continuously (e.g. in two or more stirred tank reactors operating in turn in the sequence filling, reacting and discharging) or continuously (e.g. in a (multi)-tube reactor or in a cascade of stirred tank reactors). Another possibility is to carry out the reaction in a microwave [stirred tube(s) or tube] reactor. The reaction itself is exothermic so that the (reaction) temperature may rise so rapidly that the product deteriorates whereas at too low a reaction temperature diacetyl tartaric acid anhydride may solidify. Consequently the equipment, especially for continuous processing, needs to be equipped with suitable means for a tight temperature control comprising an advanced cooling system. Therefore equipment suggested for the continuous preparation of monoglycerides is unsuitable for the preparation of the mixture of diacetyl esters of mono- and/or diglycerides according to the present invention.

In another embodiment the invention provides a process as specified above in which the reaction between diacetylated tartaric acid anhydride and mono- and diglycerides based on C12 to C22 fatty acids is carried out in a continuous manner in a suitable reactor e.g. as outlined above.

The products obtainable by the processes specified above can be finished by spray-cooling, cryogenic milling under an inert gas like liquid nitrogen, extrusion and/or taking up in a suitable extender like triglyceride or monoglycerides (known useful bakery improvers), also an anti-caking agent may be added such as e.g. calcium orthophosphate and calcium carbonate. They can be marketed directly as emulsifier, as dough conditioner, in flour and in bakery improvers (baking ingredients) for yeast-leavened baked products.

The invention also provides the use of a mixture comprising diacetylated tartaric acid esters of mono- and diglycerides based on C12 to C22 fatty acids as specified above as emulsifier, dough conditioner, in improved flour (mixes) and in bakery improvers/baking ingredients for yeast-leavened baked products.

The invention also provides baked products in which a mixture comprising diacetyl tartaric acid esters on mono- and diglycerides based of C12 to C22, preferably C16 to C18, fatty acids as specified above has been incorporated. This includes baking ingredients for baked products and more particularly for yeast-leavened products such as bread (especially white bread), tin bread, rolls, hard rolls, German crispy rolls, buns, rusks etc.

All percentages and parts mentioned herein are on a molar basis unless otherwise indicated.

The invention is illustrated by the following non-limiting examples.

EXAMPLE 1

Preparation of Purified Diacetylated Tartaric Acid Anhydride 100 g (0.67 mole) food grade L-(+)tartaric acid was slowly dosed to 250 g (2.45 moles) acetic anhydride (P.A.) in a conical flask of 500 ml capacity equipped with a reflux condenser and a magnetic stirrer. Prior to the dosing of tartaric acid, 2 microliters concentrated sulphuric acid were dosed as a catalyst. The reaction was strongly exothermic and was controlled by the dosing speed of the tartaric acid after the initial rise in temperature. The mixture was boiled under reflux conditions for approximately 15 minutes. Then the mixture was slowly cooled to ambient temperature and diacetylated tartaric acid anhydride started to crystallise at a temperature below 60–65° C.

At ambient temperature the mixture was cooled further with crushed ice to approximately 3–5° C. and is then transferred to a Buichner funnel. The funnel itself was placed under a dry $N_2$ (nitrogen) blanket to prevent hydrolysis of the diacetylated tartaric acid anhydride. The acetic acid was removed by applying vacuum to the funnel. When the acetic acid and excess acetic anhydride had been removed the white needle shaped crystals were washed three times with diethyl ether (P.A.) of 3–5° C. Finally the crystals were transferred to a rotary evaporator equipped with a 2-liter powder flask. The crystals were dried at ambient temperature at approximately 10 kPa (100 mbar) pressure. To speed up the drying process, a small flow of dry $N_2$ was led through the rotary flask. The yield was 120–125 g, which indicated an efficiency of 83–87% calculated on the tartaric acid. The white crystals were stored at 5° C. in a dark, dry place. The whole procedure was carried out twice and the white crystals obtained were combined.

Preparation of diacetyl tartaric acid esters of mono- and diglycerides.

261 g (0.75 mole) of distilled monoglyceride of mainly palmitic and stearic acid (Admul 8903K ex Quest) containing approximately 4% diglycerides were molten and 165 g (0.76 mole) of solid diacetylated tartaric acid anhydride as prepared above were added to a rotary evaporator flask and the mixture was slowly further molten using an oil bath of 120° C. for heating. After approximately 10 minutes the mixture was completely molten and 425.9 mg sodium stearate dispersed in Admul 8903K were dosed. After additional mixing for 5 minutes (total reaction time 15 minutes) the mixture was crash-cooled on a metal plate, powdered by cryogenic milled under liquid $N_2$ and sieved to over 212 micrometers and a few percents of an anti-caking agent were added. The product showed outstanding baking properties. The product obtained was analyzed by NMR and the results are shown below.

Baking experiments

Hard rolls were baked based on the following recipe:

| Ingredient | Weight (g) | Percentage (w.w.) |
|---|---|---|
| Flour (1) | 2000 | 100 |
| Water (14 C.) | 1200 | 60 |
| Bakers yeast (2) | 80 | 4.0 |
| NaCl | 40 | 2.0 |
| Diacet. tartaric (3) Ester mixture | 4 | 0.2 |

(1) wheat flour (low protein), Kolibri, ex Meneba, Rotterdam.
(2) "Koningsgist", ex Gist-Brocades, Delft, Netherlands.
(3) amount calculated as free from anti-caking agent.

Hard rolls were baked with the diacetylated tartaric ester mixture according to Example 1 and compared with hard rolls containing the same amount of a commercially available diacetylated tartaric ester of monoglyceride mixture (Admul Datem 1075, cx Quest, Naarden, Netherlands), which were finished in the same way as described above. Both ester mixtures contained tartaric acid percentages of 27% w.w.

Processing is summarized as follows: Kneading: "Kemper Spiral"; Dough temperature: 27° C.; Scaling: 1640 g; First proofing: 15 minutes in the bakery (25° C.; 60% RH); Round up: by hand; Second proofing: 15 minutes in the bakery (32° C.; 80% RH); Dividing, round up: "Record Automat"; Rest proofing: 3 minutes in the bakery (25° C.; 60% RH); Shaping: "Frilado" (rolls 5); Final proofing: 55 and 70 minutes (32° C.; 80% RH); Baking: 19 minutes 230° C. (oven program 1); on the oven floor with plenty steam.

The NMR characteristics of both ester mixtures were determined and their baking properties as well as the baked hard rolls were evaluated by a team of experienced bakers. The results obtained are summarized below.

|  | NMR data Mole % of Component A | NMR data Mole % of Component B | NMR data Mole % of Rest | Specific volume 100 = 5.50 ml/g fermentation time 55 min. | 70 min. |
|---|---|---|---|---|---|
| Example 1 | 65.6 | 21.5 | 12.9 | 113 | 108 |
| Datem 1075 | 36.3 | 54.3 | 9.4 | 100 (ref.) | 99 |

The table below provides a rating as to the dough characteristics. (+=good; ++=better; +++=best etc.)

|  | Dough Consistency | Stability 55 min. | Stability 70 min. | Oven spring 55 min. | Oven spring 70 min. | Form 55 min. | Form 70 min. |
|---|---|---|---|---|---|---|---|
| Example 1 | Extensible Stiffer Elastic | +++ | ++ | +++ | ++ | +++ | ++ |
| Datem 1075 | Extensible | ++ | − | + | − | ++ | + |

EXAMPLES 2, 3, 4, 5, 6 AND 7

Preparation of Diacetylated Tartaric Acid Anhydride 286 g (1.91 moles) food grade L-(+) tartaric acid were slowly dosed to 621 g (6.09 moles) acetic anhydride (PA.) in a conical flask of 2 liter capacity equipped with a reflux condenser and a magnetic stirrer. Prior to the dosing of tartaric acid, 5 microliters concentrated sulphuric acid were dosed as a catalyst. The reaction was strongly exothermic and was controlled by the dosing speed of the tartaric acid after the initial rise in temperature. After all the tartaric acid was dosed the mixture was transferred to a rotary evaporator and the acetic acid including the remaining acetic anhydride was distilled off under reduced pressure. The rotary flask was heated with an oil bath of approximately 140–150° C. to prevent solidification of the diacetyl tartaric anhydride obtained. The yield was approximately 410 g indicating an efficiency of 99% based on tartaric acid. The molten diacetyl tartaric anhydride could be used directly for reaction with the mono 15 and/or diglycerides.

Preparation of diacetyl tartaric acid esters of mono- and diglycerides.

A mixture of 648 g (1.85 moles) of distilled monoglyceride of (palm oil based) C16 and C18 fatty acids containing approximately 4 wt % diglycerides were molten in a 2 liter Pyrex oil jacketed reaction vessel which was heated from an oil bath to 140° C. under a dry $N_2$ blanket to prevent oxidation and to increase safety. When a temperature of 140° C. was reached an Ultra Turrax mixer immersed in the molten mixture was switched on to high speed (24 000 rpm) and diacetylated tartaric anhydride as prepared above was added in an amount of 410 g (1.90 moles) during approximately 15–20 seconds. The sodium stearate catalyst was dosed and the catalyst was quickly dispersed in Admul 8903K by the Ultra Turrax mixer, which also caused some heating. The reaction temperature was recorded with a PC using an Adam 4017 interface and Genie 2.0 software. After a reaction time of 0.5, 1, 3, 10 and 20 minutes samples were taken for analyses and evaluation. After a reaction time of 20 minutes the reaction was terminated and the different products were flaked on a metal plate at ambient temperature and subsequently powdered by cryogenic milling. The products obtained were analyzed by NMR.

Comparative Examples 1, 2 and 3 represent the data of commercial products Panodan 90, ex Grindsted, Denmark found to contain 20 wt % fat on total sample, Beldem 2500, found to contain 30% fat on total sample ex Beldem, Belgium and Abitec PX, ex Abitec, UK found to contain 30% fat on total sample respectively all of which comprise DATEM esters based on distilled monoglycerides.

Moreover an additional Example (Example 4) has been inserted in tables below. This additional Example having a reaction time of 2 minutes was based on a 60 wt % monodiglyceride (Admul MG 6203, ex Quest, Naarden, Netherlands) and was prepared by a method similar to the route described above in this Example.

These examples show that the preparation of diacetyl tartaric acid esters of mono- and diglycerides can be carried out well in high yield, e.g., by contacting molten monoglycerides with molten acetylated tartaric acid anhydride under conditions of short reaction times combined with intensive agitation which indicates that this reaction is well-suited for continuous operation e.g. in a (multi)-tube reactor.

The composition of the various reaction mixtures obtained was determined by NMR and the results are tabulated below.

|  | Reaction time | NMR mole % Comp. A | NMR mole % Comp. B | Monoglyc. Based on Approx. |
|---|---|---|---|---|
| Example 2 | 0.5 min. | 66.1 | 14.7 | 95% |
| Example 3 | 1 min. | 65.5 | 16.6 | 95% |
| Example 4 | 2 min. | 64.3 | 15.0 | 60% |
|  |  | 50.4* | 11.7* |  |
| Example 5 | 3 min. | 63.5 | 20.4 | 95% |
| Example 6 | 10 min. | 60.5 | 23.5 | 95% |
| Example 7 | 20 min. | 56.3 | 24.0 | 95° |
| Comparative Example 1 | Unknown** | 40.4<br>48.3*** | 38.3<br>45.7*** | 95% |
| Comparative Example 2 | Unknown** | 34.9<br>50.9*** | 16.1<br>23.5*** | 95% |
| Comparative Example 3 | Unknown** | 32.7<br>42.8*** | 18.4<br>24.0*** | 95% |

*corrected for diglyceride tartaric acid and triglyceride
**the reaction time is unknown because this is a competitors product
***amount calculated on basis of fat free

EXAMPLES 8, 9, 10 AND 11

Preparation of Diacetyl Tartaric Acid Esters of Mono- and Diglycerides

The procedure of Examples 2–7 described above was followed with some exceptions: the sequence order of introducing the ingredients was reversed; a blade stirrer was used; the amounts of diacetylated tartaric acid anhydride reacted were varied; the reaction time and method of cooling were changed to a reaction time of 2 minutes only and the vessel was cooled to 80° C. in approximately 3 minutes by applying water of 60° C. on a coil. These products which had excellent baking properties were flaked, subsequently powdered by cryogenic milling and sieved to over 212 micrometers and adding a few percents of an anti-caking agent.

Baking experiments

Hard rolls were baked based on the recipe given in Example 1 above. These hard rolls were baked with the diacetylated tartaric ester mixture according to Examples 8 to 11 and compared with hard rolls containing the same amount of a commercially available diacetylated tartaric esters of monoglyceride mixtures (Admul Datem 1075, based on a mono-diglyceride mixture containing 60% monoglycerides, and Admul 1972, based on 95% pure monoglycerides respectively, ex Quest, Naarden, Netherlands which were finished in the same way as described above. The ester mixtures contained diacetylated tartaric acid in varying amounts indicated in the table below. The processing details were identical to those disclosed in Example 1.

|  | Wt % tartaric acid on endproduct In ester mixture | NMR Data Mole % of comp. A | NMR data Mole % of comp. B | NMR data Mole % of the rest | Specific volume 100 = 5.5 (ml/g) fermentation time | |
|---|---|---|---|---|---|---|
|  |  |  |  |  | 55 min | 70 min |
| Example 8 | 17 | 52.8 | 6.0 | 41.2 | 110 | 110 |
| Example 9 | 21 | 56.6 | 9.4 | 34.0 | 114 | 109 |
| Example 10 | 21 | 49.8 | 22.9 | 27.3 | 114 | 111 |
| Example 11 | 27 | 64.3 | 22.4 | 13.3 | 113 | 108 |
| Datem 1972 | 23 | 42.2 | 30.3 | 27.5 | 105 | 103 |
| Datem 1075 | 27 | 36.3 | 54.3 | 9.4 | 100 | 96 |

The NMR characteristics of the ester mixtures evaluated above were determined and their baking properties as well as the baked hard rolls were evaluated by a team of experienced bakers. The results obtained are summarized below. The table below provides a rating as to the dough characteristics. (+=good; ++=better; +++=best etc.)

|  | Dough consistency | Stability 55 min. | Stability 70 min. | Oven spring 55 min. | Oven spring 70 min. | Form 55 min. | Form 70 min. |
|---|---|---|---|---|---|---|---|
| Example 8 | Less extensible, more elastic | +++ | + | ++ | + | ++ | + |
| Example 9 | Less extensible, more elastic | ++++ | ++ | ++ | + | ++ | + |
| Example 10 | Less extensible, more elastic | ++++ | ++ | ++ | + | ++ | + |
| Example 11 | Less extensible, more elastic | ++++ | ++ | ++ | + | ++ | + |
| Datem 1972 | Somewhate extensible | +++ | +(+) | ++ | + | ++ | + |
| Datem 1075 | Somewhat extensible | +++ | + | ++ | + | ++ | + |

The baking properties of Example 9, Example 11, Datem 1972 and Datem 1075 were also evaluated by baking tin bread. The recipe was as follows:

| Ingredient | Weight (g) | Percentage (w.w.) |
|---|---|---|
| Flour (1) | 2,500 | 100 |
| Water (14° C.) | 1,540 | 61.1 |
| Bakers yeast (2) | 100 | 4.0 |
| NaCl | 50 | 2.5 |
| Diacet. tartaric acid Ester mixture (3) | 5 | 0.2 |

(1) wheat flour (high protein), Kluut, ex Meneba, Rotterdam.
(2) "Koningsgist", ex Gist-Brocades, Deift, Netherlands.
(3) amount calculated as free from anti-caking agent.

Processing is summarized as: Kneading: "Tweedy"; Dough temperature: 30° C.; First proofing time: 5 minutes (32° C.; 80% RH); Dividing:"Bertrand"; 6* 656 g; Round up: by hand; Second proofing time: 6 minutes (32° C.; 80% RH); Moulding: "Opt Root" (rolls 8, 4; belt 5, 4.5); English tins; Rest proofing: 70 minutes (40° C.; 95% RH); Shock test; 50 seconds low speed (130) and 10 seconds high speed (130); Baking: 30 minutes 220/260° C. with little steam (oven program 2).

The NMR characteristics of both ester mixtures were determined and their baking properties as well as the baked tin breads were evaluated by a team of experienced bakers. The results obtained are summarized below. The table below provides a rating as to the performance characteristics.

|  | Dough consistency | Stability shock | Stability non-shock | Oven shock | Spring non-shock | Rel. spec. vol. shock | Rel. spec. vol. non-shock |
|---|---|---|---|---|---|---|---|
| Example 9 | Stiffness/dry | +++ | +++ | ++ | ++ | 105 | 106 |
| Example 11 | Less stiffness/dry | +++ | +++ | ++ | ++ | 105 | 108 |
| Datem 1972 | Somewhat extensible/dry | ++ | ++ | +(+) | ++ | 101 | 102 |
| Datem 1075 | Somewhat extensible/dry | ++ | ++ | + | ++ | 98 | 100 |

(+=good; ++=better; +++=best etc.) Baking results at 2 g ester mixture per kg flour in bread. Relative specific volume specified on the basis of 100.

What is claimed is:

1. A baked product incorporating a mixture comprising diacetyl tartaric acid esters of mono- and diglycerides derived from $C_{12}$ to $C_{22}$ fatty acids which mixture comprises diacetyl tartaric acid glycerol monoesters containing:
    (A) one fatty acid group, one diacetylated tartaric acid monoester group and a free hydroxyl group; and
    (B) one fatty acid group and two diacetylated tartaric acid monoester groups wherein:
        (i) the concentration of (A) above in the total mixture obtained by dividing the molar amount of (A) by the sum of the molar amounts of all components in the mixture and multiplying by 100 is at least 45%, and that
        (ii) the fraction obtained by dividing the molar amount of (A) above by the combined molar amounts of (A) and (B) taken together is at least 0.70.

2. A baked product according to claim 1, wherein the concentration of (A) above in the mixture obtained by dividing the molar amount of (A) by the sum of the molar amounts of all components in the mixture and multiplying by 100 is at least 50%.

3. A baked product according to claim 1, wherein the concentration of (A) above in the mixture obtained by dividing the molar amount of (A) by the sum of the molar amounts of all components in the mixture and multiplying by 100 is at least 55%.

4. A baked product according to claim 1, wherein the concentration of (A) above in the mixture obtained by dividing the molar amount of (A) by the sum of the molar amounts of all components in the mixture and multiplying by 100 is at least 60%.

5. A baked product according to claim 1, wherein the fraction obtained by dividing the molar-amount of (A) above by the combined molar amounts of (A) and (B) taken together is at least 0.72.

6. A baked product according to claim 1, wherein the fraction obtained by dividing the molar-amount of (A) above by the combined molar amounts of (A) and (B) taken together is at least 0.75.

7. A baked product according to claim 1, wherein the fraction obtained by dividing the molar-amount of (A) above by the combined molar amounts of (A) and (B) taken together is at least 0.85.

8. A baked product according to claim 1, wherein the mixture is derived from distilled monoglycerides and contains less than 5 wt. % of diacetyl tartaric esters of fatty acid diglycerides.

9. A baked product according to claim 1, wherein the mixture is derived from distilled monoglycendes and contains less than 4 wt. % of diacetyl tartaric esters of fatty acid diglycerides.

10. A baked product according to claim 1, wherein the mixture is derived from mono and diglycerides of $C_{16}$ fatty acids, $C_{18}$ fatty acids, or a mixture thereof, said fatty acids having a iodine number below 5.

11. A baked product according to claim 1, wherein the mixture has been taken up in a suitable edible extender.

12. A baked product according to claim 1, wherein the baked product is a yeast-leavened product.

13. A baked product according to claim 12, wherein said yeast-leavened product is selected from bread, tin bread, rolls, hard rolls, German crispy rolls, buns, or rusks.

* * * * *